(12) United States Patent
Levitsky et al.

(10) Patent No.: US 8,012,469 B2
(45) Date of Patent: *Sep. 6, 2011

(54) UNIVERSAL GM-CSF EXPRESSING BYSTANDER HUMAN K562 CELL LINE

(75) Inventors: Hyam I. Levitsky, Owings Mills, MD (US); Ivan Borrello, Baltimore, MD (US)

(73) Assignee: Johns Hopkins University School of Medicine, Baltimore, MD (US)

( * ) Notice: Subject to any disclaimer, the term of this patent is extended or adjusted under 35 U.S.C. 154(b) by 275 days.

This patent is subject to a terminal disclaimer.

(21) Appl. No.: 12/139,001

(22) Filed: Jun. 13, 2008

(65) Prior Publication Data

US 2008/0260758 A1  Oct. 23, 2008

Related U.S. Application Data

(60) Continuation of application No. 11/361,832, filed on Feb. 23, 2006, now Pat. No. 7,390,483, which is a division of application No. 09/992,443, filed on Nov. 16, 2001, now abandoned, which is a continuation of application No. 09/241,939, filed on Feb. 2, 1999, now Pat. No. 6,464,973.

(60) Provisional application No. 60/073,405, filed on Feb. 2, 1998.

(51) Int. Cl.
 *A61K 48/00* (2006.01)
 *A61K 39/00* (2006.01)
 *A01N 63/00* (2006.01)

(52) U.S. Cl. ............. 424/93.21; 424/93.1; 424/93.2; 424/184.1; 424/185.1

(58) Field of Classification Search .............. None
See application file for complete search history.

(56) References Cited

U.S. PATENT DOCUMENTS

| | | | |
|---|---|---|---|
| 5,574,205 A | 11/1996 | Kucherlapati et al. | |
| 5,637,483 A | 6/1997 | Dranoff et al. | |
| 5,670,148 A | 9/1997 | Sherwin et al. | |
| 5,674,486 A | 10/1997 | Sobol et al. | |
| 5,681,562 A | 10/1997 | Sobol et al. | |
| 5,705,732 A | 1/1998 | Sims et al. | |
| 5,744,347 A | 4/1998 | Wagner et al. | |
| 5,861,159 A | 1/1999 | Pardoll et al. | |
| 6,074,637 A | 6/2000 | Roth et al. | |
| 6,171,597 B1 | 1/2001 | Maass et al. | |
| 6,348,352 B1 | 2/2002 | Shepard et al. | |
| 6,464,973 B1 | 10/2002 | Levitsky et al. | |
| 6,521,449 B1 | 2/2003 | Polack et al. | |
| 7,390,483 B2 * | 6/2008 | Levitsky et al. | 424/93.21 |

FOREIGN PATENT DOCUMENTS

| | | |
|---|---|---|
| WO | WO 91/01140 A1 | 2/1991 |
| WO | WO 93/07906 A1 | 4/1993 |
| WO | WO 96/33746 A1 | 10/1996 |

OTHER PUBLICATIONS

Borrello et al., "Description of a universal GM-CSF-producing bystander cell for use in autologous tumor cell vaccine formulations," *Blood*, 92 (10): Suppl. 1 part 1-2: (1998).

Borrello et al., "A universal granulocyte-macrophage colony-stimulating factor-producing bystander cell line for use in the formulation of autologous tumor cell-based vaccines," *Human Gene Therapy*, 10: 1983-1991 (1999).

Clay et al., "Potential use of T cell receptor genes to modify hematopoietic stem cells for the gene therapy of cancer," *Pathology Oncology Research*, 5(1): 3-15 (1999).

Dictionary.com/naturally, 2008.

Dranoff et al., "Vaccination with irradiated tumor cells engineered to secrete murine granulocyte-macrophage colony-stimulating factor simulates potent, specific, and long-lasting anti-tumor immunity," *Proc. Natl. Acad. Sci.* USA, 90 (8): 3539-3543 (1993).

Ferrone et al., "Loss of HLA class I antigens by melanoma cells: molecular mechanisms, functional significance and clinical relevance," *Immunol Today*, 16: 487-494 (1995).

Golumbek et al., "Controlled release. Biodegradable cytokine depots: A new approach in cancer vaccine design," *Cancer Research*, 53: 5841-5844 (1993).

Huang et al., "Role of bone marrow-derived cells in presenting MHC class 1-restricted tumor antigens," *Science*, 264: 961-965 (1994).

Hwang et al., "Prostate cancer vaccines: current status," *Seminars in Oncology*, 26 (2): 92-201 (1999).

Jaffee et al., "Use of murine models of cytokine-secreting tumor vaccines to study feasibility and toxicity issues critical to designing clinical trials," *Journal of Immunotherapy*, 18(1): 1-9 (1995).

Janeway et al., "*Immunobiology, The immune system in health and disease*," Garland Publishing, Inc., 1, 24-25 (1994).

Klein et al., "Properties of the K562 cell line, derived from patient with chronic Myeloid leukemia," *Int. J. Cancer*, 18 (4): 421-431 (1976).

Levitsky et al., "In vivo priming of two distinct antitumor effector populations: the role of MHC class I expression," *J. Exp. Med.*, 179 (4): 1215-1224 (1994).

Levitsky et al., "Immunization with granulocyte-macrophage colony-stimulating factor-transduced, but no B7-1-transduced, lymphoma cells primes idiotyoe-specific T cells and generates potent systemic antitumor immunity," *The Journal of Immunology*, 156(1): 3858-3865 (1996).

Lozzio et al., "Human Chronic Myelogenous Leukemia Cell-Line With Positive Philadelphia Chromosome," *Blood*, 45 (3): 321-334 (1975).

Mackensen et al., "Induction of tumor-specific cytotoic T lymphocytes by immunization with autologous tumor cells and Interleukin-2 gene transfected fibroblasts," *Journal of Molecular Medicine*, 75 (4): 290-296 (1997).

Ockert et al., "Advances in cancer immunotherapy," *Imunology Today*, 20 (2): 63-65 (1999).

(Continued)

*Primary Examiner* — Q Janice Li

(74) *Attorney, Agent, or Firm* — Barnes & Thornburg LLP

(57) ABSTRACT

The present invention provides a universal immunomodulatory cytokine-expressing bystander cell line, a composition comprising such a cell line and a cancer antigen, a method of making such a cell line, and a method of using such a composition.

17 Claims, 4 Drawing Sheets

OTHER PUBLICATIONS

Owen-Schaub et al., "Wild-type human p53 and a temperature-sensitive mutant induce fas/APO-1 expression," *Molecular and Cellular Biology*, 15 (6): 3032-3040 (1995).

Parker et al., "Transplantation of discordant xenografts: a challenge revisited," *Immunology Today*, 17 (8): 373-378 (1996).

Porgador et al., "Interleukin-6 gene transfection into Lewis lung carcinoma cancer cells suppresses the malignant phenotype and confers immunotherapeutic competence against parental metastatic cells," *Cancer Research*, 52: 3679-3686 (1992).

Sanda et al., "Demonstration of a rational strategy for human prostate cancer gene therapy," *The Journal of Urology*, 151: 622-628 (1994).

Simons et al., "Bioactivity of autologous irradiated renal cell carcinoma vaccines generated by ex Vivo granulocyte-macrophage colony-stimulating factor gene transfer," *Cancer Research*, 57: 1537-1546 (1997).

Takamura et al., "Effect of verpamil on the class I major histocompatibility complex antigen expression in K562 chronic myelogenous leukemia cells treated with recombinant human interferon-gamma," *Cancer Letters*, 65 (2): 99-106 (1992).

Thomas et al., "Enhanced tumor protection by granulocyte-macrophage colony-stimulating factor expression," *Human Gene Therapy*, 9: 835-843 (1998).

Verma et al., "Gene therapy—promises, problems, (1997), and prospects," *Nature*, 389: 239-242 (1997).

Watson et al., "Recombinant DNA," $2^{nd}$ Ed., Scientific American Books, New York, p. 218 (1992).

Wang et al., "Lack of HLA class I antigen expression by melanoma cells SK-MEL-33 caused by a reading frameshift in beta-2 microglobulin messenger RNA," *J. Clin. Invest*, 91 (2): 684-692 (1993).

Winchester et al., "Expression of Ia-Like Antigens on Cultured Malignant Melanoma Cell Lines," *PNAS*, 75 (12): 6235-6239 (1978).

* cited by examiner

ND MUG-CSF EXPRESSING
BYSTANDER HUMAN K562 CELL LINE

CROSS-REFERENCE TO RELATED PATENT APPLICATIONS

This application is a continuation of U.S. Ser. No. 11/361,832, filed Feb. 23, 2006, now issued as U.S. Pat. No. 7,390,483, which is a divisional of U.S. Ser. No. 09/992,443, filed Nov. 16, 2001, now abandoned, which is a continuation of U.S. Ser. No. 09/241,939, filed Feb. 2, 1999, now issued as U.S. Pat. No. 6,464,973, which claims the benefit of U.S. Ser. No. 60/073,405, filed Feb. 2, 1998, all of which are herein incorporated by reference in their entirety.

TECHNICAL FIELD OF THE INVENTION

The present invention relates to a universal immunomodulatory cytokine-expressing bystander cell line, a composition comprising such a cell line and a cancer antigen, a method of making such a cell line, and a method of using such a composition.

BACKGROUND OF THE INVENTION

Cancer immunotherapy is a therapeutic treatment of cancer. It is based on the premise that the failure of the immune system to reject spontaneously arising tumors is related to the failure of the immune system to respond appropriately to tumor antigens. In a functioning immune system, tumor antigens are processed and expressed on the cell surface in the context of major histocompatibility complex (MHC) class I and II molecules, which, in humans, are also referred to as "human leukocyte associated" (HLA) molecules. When complexed to antigens, the MHC class I and II molecules are recognized by $CD8^+$ and $CD4^+$ T-cells, respectively. This recognition generates a set of secondary, cellular signals and the paracrine release of specific cytokines or soluble so-called "biological response modifiers" that mediate interactions between cells and stimulate host defenses to fight off disease. The release of cytokines then results in the proliferation of antigen-specific T-cells.

Active immunotherapy involves the injection of cancer or tumor cells to generate either a novel or an enhanced systemic immune response. The tumor cells employed can be autologous, i.e., derived from the host to be treated, or allogeneic, i.e., derived from a host other than the one to be treated. Such a strategy is referred to as a "vaccine," meaning use of an antigen source, such as an intact cancer or tumor cell, to stimulate an immune response against established metastatic cancer—not prophylactic immunization.

The use of autologous tumor cells as "vaccines" to augment anti-tumor immunity has been extensively investigated (Oettgen et al., in Biologic Therapy of Cancer, DeVita et al., eds. (Lippincott, Philadelphia, Pa.), pp. 87-119 (1991)). Although a few patients appear to have benefited from autologous cancer vaccines, their use has only realized partial and short-lived results. Thus, numerous attempts have been made to improve the efficacy of cancer vaccines. Such attempts include radiation and/or chemical modification, infection of autologous tumor cells with virus prior to reinjection into a patient, and transfection/transduction of the tumor cells with genes encoding immunologically relevant molecules, such as cytokines or T-cell co-stimulatory molecules. These attempts, which have been initially explored in murine tumor models, have demonstrated the ability to prime systemic immune responses capable of mediating the rejection of micrometastatic tumors at distant sites. Analysis of the mechanisms of the anti-tumor immune responses generated through such vaccination has underscored the importance of the T-cell arm of the immune system in tumor rejection. Nonspecific immunostimulants also have been used, although little improvement has been realized.

At the clinical level, transfection/transduction of tumor cells with genes encoding immunologically relevant molecules involves tumor resection, culture of cells isolated from the tumor, transfection/transduction of the cultured tumor cells with a gene encoding an immunologically relevant molecule, such as a cytokine, e.g., GM-CSF, irradiation of the transfected/transduced tumor cells, and administration of the irradiated tumor cells to the patient. Tumor cells that have been genetically modified to express various factors, such as IL-4, IL-2, IFN-γ, TNF-α, G-CSF, JE, IL-7 and IL-6, have been shown to lead to rejection of the genetically modified cells in syngeneic hosts (Tepper et al., Cell 57: 503-512 (1989); Li et al., Mol. Immunol. 27: 1331-1337 (1990); Golumbek et al., Science 254: 713-176 (1991); Fearon et al., Cell 60: 397-403 (1990); Gansbacher et al., J. Exp. Med. 172: 1217-1224 (1990); Gansbacher et al., Cancer Res. 50: 7820-7825 (1990); Watanabe et al., PNAS USA 86: 9456-9460 (1989); Asher et al., J. Immunol. 146: 3227-3234 (1991); Blankenstein et al., J. Exp. Med. 173: 1047-1052 (1991); Teng et al., PNAS USA 88: 3535-3539 (1991); Colombo et al., J. Exp. Med. 173: 889-897 (1991); Rollins et al., Mol. Cell. Biol. 11: 3125-3131 (1991); Hock et al., J. Exp. Med. 174: 1291-1298 (1991); Aoki et al., PNAS USA 89: 3850-3854 (1992); Porgador et al., Cancer Res. 52: 3679-3686 (1992)). Systemic immunity has been demonstrated to increase with cells that express IL-4, IL-2, IFN-γ, TNF-α, IL-7 or IL-6 (Golumbek et al. (1991), supra; Porgador et al. (1992), supra).

Various studies comparing irradiated, cytokine-transduced autologous tumor cells have demonstrated that GM-CSF-transduced autologous tumor cells are the most potent inducers of long-lasting, specific tumor immunity (Dranoff et al., PNAS USA 90: 3539-3543 (1993); see, also, Asher et al., J. Immunol. 146: 3327-3334 (1990); Sanda et al., J. of Urology 151: 622-628 (1994); Simons et al., Cancer Research 57: 1537-1546 (1997)). The efficacy of GM-CSF-transduced vaccines has been demonstrated in preclinical models of melanoma, lymphoma, and cancers of the lung, colon, kidney and prostate (Dranoff et al. (1990), supra; Golumbek et al. (1991), supra; Sanda et al. (1994), supra; Jaffee et al., J. Immunother. 18: 1-9 (1995); Caducci et al., Cancer (Phila.) 75: 2013-2020 (1995); Vieweg et al., Cancer Res. 54: 1760-1765 (1994); Jaffee et al., J. Immunother. 19: 1-8 (1996); Levitsky et al., J. Immunol. 156: 3858-3865 (1996)). At the site of vaccination, GM-CSF locally activates (paracrine) antigen-presenting cells (APCs), including dendritic cells and macrophages. APCs subsequently prime $CD4^+$ and $CD8^+$ T-cells, which recognize tumor-associated antigens at metastatic sites, thereby mediating systemic antitumor immunity.

A number of phase-I clinical trials in patients with metastatic cancer have taken place. At Johns Hopkins University, patients with metastatic renal cell carcinoma were treated either with unmodified irradiated autologous tumor cells or irradiated autologous tumor cells transduced to secrete GM-CSF. Measured parameters of immunity paralleled what had been seen in the mouse models and the randomization enabled a clear demonstration of the role of GM-CSF as a molecular adjuvant. A subsequent trial in the treatment of patients with metastatic prostate cancer with autologous GM-CSF-transduced tumor cells extended these observations. Ongoing is a trial at the Dana Farber Cancer Institute in which patients with metastatic melanoma are being treated with autologous GM-CSF-transduced tumor cells.

The pilot studies at Johns Hopkins University and the Dana Farber Cancer Institute and elsewhere have lent support to the use of irradiated, cytokine-transduced autologous tumor vaccines as a therapeutic method of treatment. For many malignancies, large numbers of autologous tumor cells are easily obtained at presentation prior to surgery or chemotherapy-induced remission. For diseases such as acute or chronic leukemias, lymphoma, and colonic carcinoma, well over $5 \times 10^9$ tumor cells can be obtained and stored with methodologies currently in use at most cancer treatment centers. However, the need for in vitro culture to enable gene transfer and the inability to obtain reproducibly and uniformly high levels of GM-CSF production through such procedures limits this therapeutic approach.

In order to circumvent this problem, a number of investigators are conducting studies of immunization with irradiated, GM-CSF-transfected allogeneic tumor cell lines, such as in the treatment of prostate and pancreatic cancer. The rationale for this approach is that the relevant tumor antigen(s) may be shared between the immunizing allogeneic tumor cell line and the tumor of the patient who is being immunized. Given that the relevant tumor antigens have not been defined in most of these systems, this assumption remains as yet unproven.

In view of the above, materials and methods that would obviate the need for in vitro culture for purposes of gene transfer to autologous tumor cells and that would enable reproducible and uniform immunomodulatory cytokine, e.g., GM-CSF, production would be highly desirable. Therefore, it is an object of the present invention to provide such materials and methods. This and other objects and advantages will become apparent from the detailed description provided herein.

BRIEF SUMMARY OF THE INVENTION

The present invention provides a universal immunomodulatory cytokine-expressing bystander cell line. The universal bystander cell line is a human cell line, which either naturally lacks major histocompatibility class I (MHC-I) antigens and major histocompatibility class II (MHC-II) antigens or is modified so that it lacks MHC-I antigens and MHC-II antigens. In addition, the universal bystander cell line is modified by introduction of a nucleic acid molecule comprising a nucleic acid sequence encoding an immunomodulatory cytokine operably linked to a promoter. Preferably, the immunomodulatory cytokine is granulocyte macrophage-colony stimulating factor (GM-CSF). The universal bystander cell line expresses preferably at least about 500 ng, more preferably at least about 1,000 ng, GM-CSF/$10^6$ cells/24 hours. Alternatively and also preferably, the immunomodulatory cytokine is interleukin 2 (IL-2). Preferably, the human cell line is characterized by the absence of B-lymphocyte markers of immunoglobulin, an Epstein-Barr virus (EBV) genome and an associated nuclear antigen, and receptors for EBV. A preferred human cell line is one that is derived from a blast crisis of chronic myeloid leukemia. An example of a preferred cell line is K562. Preferably, the universal bystander cell line grows in defined, i.e., serum-free, medium. The promoter to which the nucleic acid sequence encoding an immunomodulatory cytokine is operably linked is preferably a cytomegalovirus promoter. Preferably, the universal bystander cell line further comprises a nucleic acid sequence encoding hygromycin resistance operably linked to a promoter and is selected by growth in culture medium comprising at least about 400 µg/ml hygromycin, preferably followed by growth in culture medium comprising at least about 1,000 µg/ml hygromycin.

Also provided by the present invention is a composition comprising the universal bystander cell line and a cancer antigen. A method of making a universal immunomodulatory cytokine-expressing bystander cell line is also provided, as well as a method of stimulating an immune response to a cancer in a human patient.

DETAILED DESCRIPTION OF THE INVENTION

Figure 1:
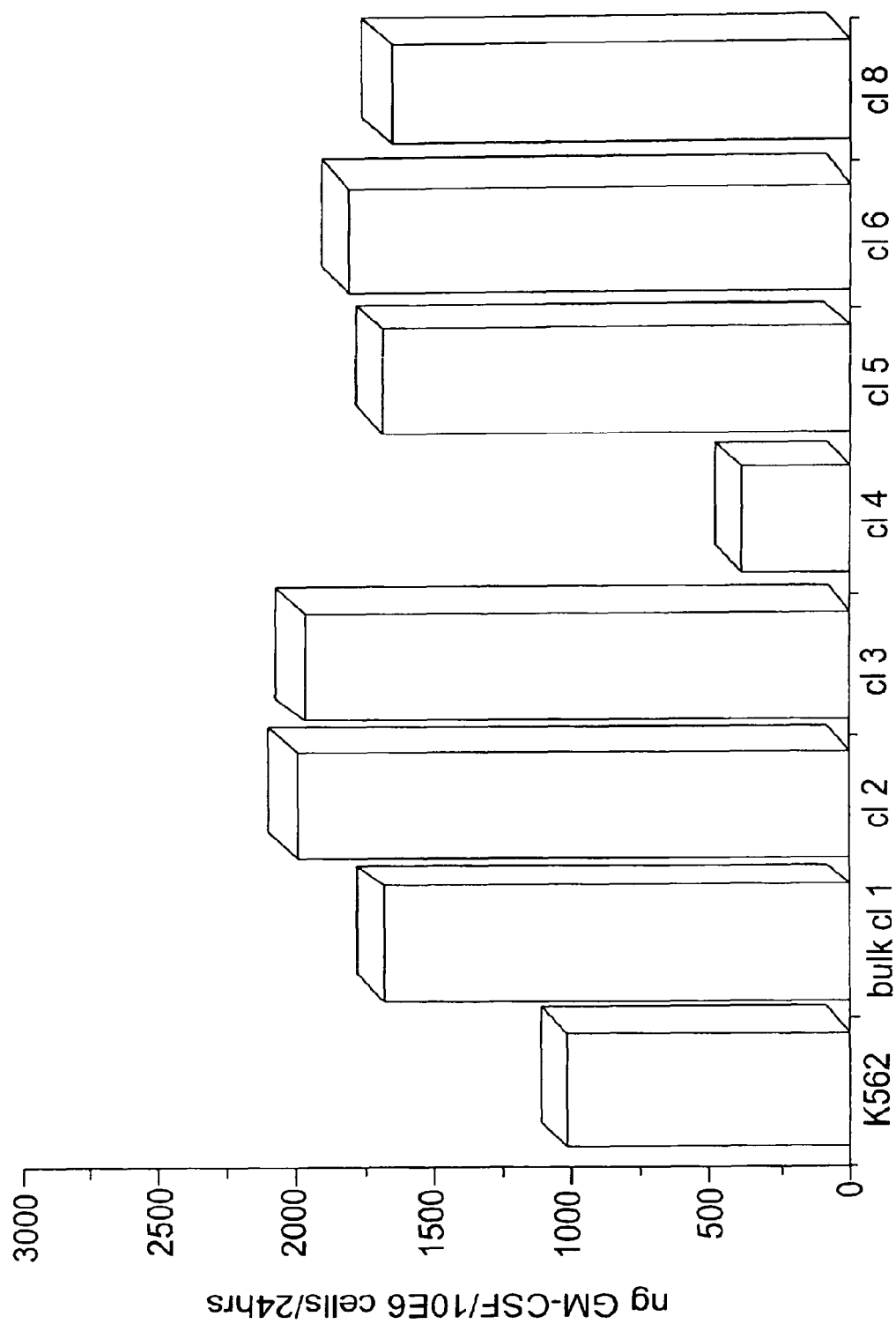
FIG. 1 is a bar graph of ng GM-CSF/$10^6$ cells/24 hrs versus cell line.

The present invention is predicated on the observation that, in the context of a cancer vaccine, the cancer cell, itself, need not directly produce an immunomodulatory cytokine, such as GM-CSF, in order to stimulate an immune response against the cancer cell. The present invention is further predicated on the surprising and unexpected discovery that a universal bystander cell line, which can locally produce an immunomodulatory cytokine, such as GM-CSF, at unprecedented high levels, can be made. The present invention is advantageous in that, through the administration to a patient of a composition comprising the universal bystander cell and an autologous cancer antigen, e.g., an autologous tumor cell, paracrine production of an immunomodulatory cytokine, such as GM-CSF, adequate recruitment of APCs, and successful priming against the cancer antigens are achieved, thereby obviating the need to culture and transduce autologous tumor cells for each and every patient and to contend with variable and, oftentimes, inefficient transduction efficiencies.

In view of the above, the present invention provides a universal, immunomodulatory cytokine-producing bystander cell line. The cell line is a mammalian, preferably a human, cell line, which naturally lacks major histocompatibility class I (MI-IC-I) antigens and major histocompatibility class II (MHC-II) antigens or is modified so that it lacks MHC-I antigens and MHC-II antigens. Theoretically, any mammalian, preferably human, cell line that is capable of paracrine production of an immunomodulatory cytokine can be used. The human cell line preferably is characterized by the absence of B-lymphocyte markers of immunoglobulin, an Epstein-Barr virus (EBV) genome and an associated nuclear antigen, and receptors for EBV. A preferred human cell line is one that is derived from a blast crisis of chronic myeloid leukemia. An example of a preferred human cell line is K562 (ATCC CCL-243; Lozzio et al., Blood 45(3): 321-334 (1975); Klein et al., Int. J. Cancer 18: 421-431 (1976)). The universal bystander cell line preferably grows in defined, i.e., serum-free, medium. In addition, the universal bystander cell line preferably grows as a suspension.

Cells that lack MHC-I antigens can be achieved by interfering with the expression and/or transport of the α chain. Cells that lack MHC-II antigens can be achieved by interfering with expression and/or transport of the α and β chains.

Inactivation of MHC-I and -II antigens can be achieved in a variety of ways (see, for example, U.S. Pat. No. 5,574,205). For example, a "dominant negative" can be created. A single modified $\beta_2$ microglobulin gene, whose protein product effectively complexes with MHC-I molecules and acts as a decoy, thereby preventing the insertion of MHC-I antigens into the membrane, can be overexpressed. A similar approach can be used with respect to MHC-II antigens by overexpressing modified genes encoding defective α or β subunits that complex with the host cells' subunits rendering them nonfunctional. Transfection, retroviral infection or homologous recombination can be used to achieve expression of modified MHC or $\beta_2$ microglobulin genes or inactivation of genes.

Levels of MHC-I antigen on the cell surface can be reduced by introducing into cells a sequence encoding adenoviral E19 protein by transfection or retroviral infection. The protein forms complexes specifically with MHC-I antigens in the rough endoplasmic reticulum preventing normal transport of MHC-I molecules to the plasma membrane (Andersson et al., Cell 43: 215-222 (1985); Pabo et al., Advances in Cancer Research 42: 151-163 (1989)).

In addition to lacking MHC-I and MHC-II antigens or being modified to lack MHC-I and MHC-II antigens, the mammalian, preferably human, cell line is modified by introduction of a nucleic acid molecule comprising a nucleic acid sequence encoding an immunomodulatory cytokine operably linked to a promoter.

By "modified" is meant the provision to the universal bystander cell line of a nucleic acid molecule, e.g., vector, that comprises a nucleic acid sequence encoding a cytokine that either is not expressed in the cell line or, as a result of the provision of the nucleic acid molecule, is now expressed at a greater level. A "vector" encompasses a DNA molecule, such as a plasmid, virus or other vehicle, which contains one or more heterologous or recombinant DNA sequences, e.g., a cytokine gene or cytokine coding sequence of interest under the control of a functional promoter and possibly also an enhancer, and that is capable of functioning as a vector as that term is understood by those of ordinary skill in the art.

Any suitable vector can be employed that is appropriate for introduction of nucleic acids into eukaryotic cells, or more particularly animal cells, such as mammalian, e.g., human, cells. Preferably, the vector is compatible with the cell, e.g., is capable of imparting expression of the cytokine gene or coding sequence, and is stably maintained or relatively stably maintained in the cell. Desirably, the vector comprises an origin of replication. When a cytokine coding sequence is transferred (i.e., as opposed to a cytokine gene having its own promoter), optimally the vector also contains a promoter that is capable of driving expression of the coding sequence and that is operably linked to the coding sequence. A coding sequence is "operably linked" to a promoter (e.g., when both the coding sequence and the promoter together constitute a native or recombinant cytokine gene) when the promoter is capable of directing transcription of the coding sequence.

Appropriate viral vectors include, but are not limited to simian virus 40, bovine papilloma virus, Epstein-Barr virus, adenovirus, herpes virus, vaccinia virus, Moloney murine leukemia virus, Harvey murine sarcoma virus, murine mammary tumor virus, and Rous sarcoma virus. Any plasmid suitable for use in a eukaryote, in particular a mammal, e.g., a human, can be used in the context of the present invention. Desirably, the plasmid comprises a promoter, such as the cytomegalovirus promoter, an origin of replication, such as the SV40 origin of replication, a selectable marker, such as antibiotic resistance, and provides for mRNA with poly A tails. A preferred example of a plasmid is pCEP4 (See Example 1).

Reference to a vector or other DNA sequences as "recombinant" merely acknowledges the linkage of DNA sequences which are not typically conjoined as isolated from nature. A "gene" is any nucleic acid sequence coding for a protein or a nascent mRNA molecule. Whereas a gene comprises coding sequences and non-coding (e.g., regulatory) sequences, a "coding sequence" does not include any non-coding DNA. A "promoter" is a DNA sequence that directs the binding of RNA polymerase and thereby promotes RNA synthesis. "Enhancers" are cis-acting elements of DNA that stimulate or inhibit transcription of adjacent genes. An enhancer that inhibits transcription also is termed a "silencer." Enhancers differ from DNA-binding sites for sequence-specific DNA binding proteins found only in the promoter (which also are termed "promoter elements") in that enhancers can function in either orientation, and over distances of up to several kilobase pairs (kb), even from a position downstream of a transcribed region.

As used herein, cytokine "gene" or "coding sequence" includes cytokine genomic or cDNA sequences, greater and lesser sequences and mutations thereof, whether isolated from nature or synthesized in whole or in part, as long as the gene or coding sequence can express a protein having the characteristic function of the cytokine, i.e., the ability to stimulate the host immune response. The means of modifying genes or coding sequences are well-known in the art, and also can be accomplished by means of commercially available kits (e.g., New England Biolabs, Inc., Beverly, Mass.; Clontech, Palo Alto, Calif.). The cytokine gene or coding sequence can be of any suitable source, e.g., a mammalian species such as a human. Preferably, however, the cytokine gene or coding sequence comprises a GM-CSF sequence, particularly a human GM-CSF gene or coding sequence, including a human GM-CSF cDNA sequence (e.g., as described by Cantrell et al., PNAS USA 82: 6250-6254 (1985)).

Preferably, all proper transcription, translation and processing signals (e.g., splicing and polyadenylation signals) are correctly arranged on the vector such that the cytokine gene or coding sequence will be appropriately transcribed and translated in the cell into which it is introduced. The manipulation of such signals to ensure appropriate expression in host cells is well within the knowledge and expertise of the ordinary skilled artisan. Whereas a cytokine gene is controlled by (i.e., operably linked to) its own promoter, another promoter, including a constitutive promoter, such as, for instance the adenoviral type 2 (Ad2) or type 5 (Ad5) major late promoter (MLP) and tripartite leader, the cytomegalovirus (CMV) immediate early promoter/enhancer, the Rous sarcoma virus long terminal repeat (RSV-LTR), and others, can be employed to command expression of the cytokine coding sequence. The CMV promoter is a preferred promoter.

Alternately, a tissue-specific promoter (i.e., a promoter that is preferentially activated in a given tissue and results in expression of a gene product in the tissue where activated) can be used in the vector. Such promoters include, but are not limited to, the elastase I gene control region, which is active in pancreatic acinar cells as described by Swift et al., Cell 38: 639-646 (1984) and MacDonald, Hepatology 7: 425-515 (1987); the insulin gene control region, which is active in pancreatic beta cells as described by Hanahan, Nature 315: 115-122 (1985); the hepatocyte-specific "promoter for albumin or a.sub.1-antitrypsin described by Frain et al., Mol. Cell. Biol. 10: 991-999 (1990), and Ciliberto et al., Cell 41: 531-540 (1985); and the albumin and alpha.sub.1-antitrypsin gene control regions, which are both active in liver as described by Pinkert et al., Genes and Devel. 1: 268-276 (1987), and Kelsey et al., Genes and Devel. 1: 161-171 (1987).

Similarly, a tumor-specific promoter, such as the carcinoembryonic antigen for colon carcinoma described by Schrewe et al., Mol. Cell Biol. 10: 2738-2748 (1990), can be used in the vector. Along the same lines, promoters that are selectively activated at different developmental stages (e.g., globin genes are differentially transcribed in embryos and adults) can be employed for gene therapy of certain types of cancer.

Another option is to use an inducible promoter, such as the IL-8 promoter, which is responsive to TNF, or the 6-16 promoter, which is responsive to interferons, or to use other similar promoters responsive to other cytokines or other factors present in a host or that can be administered exogenously. Use of a cytokine-inducible promoter has the added advantage of allowing for auto-inducible expression of a cytokine gene. According to the invention, any promoter can be altered by mutagenesis, so long as it has the desired binding capability and promoter strength.

Various methods can be employed for delivering a nucleic acid molecule, e.g., a vector, to a cell in vitro. For instance, such methods include electroporation, membrane fusion with liposomes, high velocity bombardment with DNA-coated microprojectiles, incubation with calcium phosphate-DNA precipitate, DEAE-dextran mediated transfection, infection with modified viral nucleic acids, direct microinjection into single cells, and the like. Other methods are available and are known to those skilled in the art.

If the universal bystander cell line is to be used in the context of cancer immunotherapy, the immunomodulatory cytokine is one that stimulates an immune response against a cancer cell or a cancer antigen, i.e., any protein, carbohydrate or other component capable of eliciting an immune response. An inhibitory cytokine or a cytokine that prevents priming cannot be used in the context of cancer immunotherapy. While the nucleic acid molecule preferably encodes a single immunomodulatory cytokine, the nucleic acid molecule can encode two or more immunomodulatory cytokines, such as cytokines that act synergistically.

Examples of suitable immunomodulatory cytokines include interferons (e.g., IFNα, IFNβ and IFNγ), interleukins (e.g., IL-1, IL-2, IL-3, IL-4, IL-5, IL-6, IL-7, IL-8, IL-9, IL-10 and IL-12), tumor necrosis factors (e.g., TNFα and TNFβ), erythropoietin (EPO), FLT-3 ligand, macrophage colony stimulating factor (M-CSF), granulocyte colony stimulating factor (G-CSF), and granulocyte-macrophage colony stimulating factor (GM-C SF). The most preferred immunomodulatory cytokine is GM-CSF, such as human GM-CSF. An alternatively preferred immunomodulatory cytokine is IL-2.

Desirably, the universal bystander cell line expresses unprecedented high levels of an immunomodulatory cytokine, which preferably is GM-CSF. Preferably, the universal bystander cell line expresses at least about 500 ng GM-CSF/$10^6$ cells/24 hours. More preferably, the universal bystander cell line expresses at least about 1,000 ng GM-CSF/$10^6$ cells/24 hours.

For purposes of identification and selection, preferably the nucleic acid molecule comprising a nucleic acid sequence encoding an immunomodulatory cytokine operably linked to a promoter further comprises a nucleic acid sequence encoding a selectable marker operably linked to a promoter. Preferably, the selectable marker is an antibiotic resistance gene, such as hygromycin resistance. When the selectable marker is hygromycin resistance, preferably the universal bystander cell line is selected by growth in a culture medium comprising at least about 400 µg/ml hygromycin, more preferably at least about 1,000 µg/ml hygromycin.

In addition to the above, the present invention provides a composition comprising the above-described universal bystander cell line and a cancer antigen. The cancer antigen can be a cancer cell or a cancer cell-surface antigen, such as one that has been recombinantly produced or immunoprecipitated. Preferably, the cancer antigen is a cancer cell, the isolation and culture of which is within the skill in the art (see, e.g., WO 97/24132, in particular Example 4). A cell-surface antigen can be used instead of a cell when the cell-surface antigen has been identified and characterized and has been determined to induce an anti-cancer immune response. In this regard, the universal bystander cell line can be genetically modified to express a cancer antigen. For example, the bystander cell can be genetically modified to express MAGE for the treatment of melanoma, ras for the treatment of pancreatic cancer, and BCR-ABL for the treatment of chronic myelogenous leukemia.

A composition or implant appropriate for administration in vivo can comprise appropriate carriers or diluents, which further can be pharmaceutically acceptable. The means of making such a composition or an implant have been described in the art, see, for instance, Remington's Pharmaceutical Sciences, 16th Ed., Mack, ed. (1980). Use of a balanced salt solution, such as Hanks' balanced salt solution, is preferred in the composition.

In pharmaceutical dosage form, a composition can be used alone or in appropriate association, as well as in combination, with other pharmaceutically active compounds as are known in the art.

A composition of the present invention can be provided in unit dosage form, wherein each dosage unit contains a predetermined amount of the composition, alone or in appropriate combination with other active agents. The term "unit dosage form" as used herein refers to physically discrete units suitable as unitary dosages for human and other mammalian subjects, each unit containing a predetermined quantity of the composition of the present invention, alone or in combination with another active agent, calculated in an amount sufficient to produce the desired effect, in association with a pharmaceutically acceptable diluent, carrier, or vehicle, where appropriate. The specifications for the novel unit dosage forms of the present invention depend on the particular pharmacodynamics associated with the pharmaceutical composition in the particular host.

The present invention also provides a method of making a universal immunomodulatory cytokine-expressing bystander cell line. In one embodiment, the method comprises (i) obtaining a mammalian, preferably a human, cell line that does not express MHC-I antigens and MHC-II antigens, (ii) modifying the mammalian, preferably human, cell line by introducing into the mammalian, preferably human, cell line a nucleic acid molecule comprising a nucleic acid sequence encoding an immunomodulatory cytokine operably linked to a promoter and a nucleic acid sequence encoding a selectable marker operably linked to a promoter, and (iii) using the selectable marker to isolate cells that produce at least about 500 ng of said immunomodulatory cytokine/06 cells/24 hours. In another embodiment, the method comprises (i) obtaining a mammalian, preferably human, cell line, (ii) modifying the mammalian, preferably human, cell line so that it does not express MHC-I antigens and MHC-II antigens, (iii) further modifying the mammalian, preferably human, cell line by introducing into the mammalian, preferably human, cell line a nucleic acid molecule comprising a nucleic acid sequence encoding an immunomodulatory cytokine operably linked to a promoter and a nucleic acid sequence encoding a selectable marker operably linked to a promoter; and (iv) using the selectable marker to isolate cells that produce at least about 500 ng of said immunomodulatory cytokine/$10^6$ cells/24 hours.

The nucleic acid molecule comprising a nucleic acid sequence encoding an immunomodulatory cytokine operably linked to a promoter and a nucleic acid sequence encoding a selectable marker operably linked to a promoter can be any nucleic acid molecule suitable for gene transfer as described above. The retroviral MFG vector, which is described in U.S. Pat. No. 5,637,483, allows for rapid screening of a large number of potential immunomodulators for systemic immunity effects and assessment of the activity of complex combinations of molecules. It also provides high titer and high gene expression. Other retroviral vectors that can be used include pLJ, pEm and aSGC (see U.S. Pat. No. 5,637,483, in particular Example 12). Any immunomodulatory cytokine that stimulates an anti-tumor immune response can be used (see U.S. Pat. No. 5,637,483 for assays). The most preferred immunomodulatory cytokine is GM-CSF. An alternatively preferred immunomodulatory cytokine is IL-2. While any selectable marker can be used, preferably the selectable marker is an antibiotic resistance gene, such as hygromycin resistance, in which case the modified mammalian, preferably human, cell line is cultured in culture medium comprising at least about 400 µg hygromycin/ml culture medium. More preferably, the modified mammalian, preferably human, cell line is subsequently cultured in culture medium comprising at least about 1,000 µg hygromycin/ml culture medium. The culture medium preferably is defined, i.e., serum-free. A preferred promoter for expression of the immunomodulatory cytokine in the method is a cytomegalovirus promoter.

Further provided by the present invention is a method of stimulating an immune response to a cancer in a mammalian, preferably a human, patient. Desirably, the method effects a systemic immune response, i.e., a T-cell response, to the cancer. The method comprises administering to the patient the above-described composition, wherein the universal bystander cell line is derived from a mammalian, preferably human, cell line, the cancer antigen is an antigen of the cancer in the patient, and the composition is rendered proliferation incompetent, such as by irradiation. Upon administration of the composition, an immune response to the cancer is stimulated.

"Administering" means the actual physical introduction of the composition into the host. Any and all methods of introducing the composition into the host are contemplated according to the invention; the method is not dependent on any particular means of introduction and is not to be so construed. Means of introduction are well-known to those skilled in the art, and also are exemplified herein.

Any suitable route of administration can be used. Preferably, the composition is administered subcutaneously or intratumorally. One skilled in the art will recognize that, although more than one route can be used for administration, a particular route can provide a more immediate and more effective reaction than another route. Local or systemic delivery can be accomplished by administration comprising application or instillation of the formulation into body cavities, inhalation or insufflation of an aerosol, or by parenteral introduction, comprising intramuscular, intravenous, intraportal, intrahepatic, peritoneal, subcutaneous, or intradermal administration. In the event that the tumor is in the central nervous system, the composition must be administered intratumorally because there is no priming of the immune system in the central nervous system.

Desirably, the immunomodulatory cytokine is derived from a human, although a cytokine from a nonhuman source can be used if it is substantially homologous to the human cytokine and has been demonstrated to exhibit similar activity. Preferably, the cancer antigen is a cell of the cancer to be treated, i.e., an autologous cancer cell. If the composition is rendered proliferation—incompetent by irradiation, typically, the universal bystander cells and the cancer cells are plated in a tissue culture plate and irradiated at room temperature using a.sup.137CS source. Preferably, the cells are irradiated at a dose rate of from about 50 to about 200 rads/min, even more preferably, from about 120 to about 140 rads/min. Preferably, the cells are irradiated with a total dose sufficient to inhibit the majority of cells, i.e., preferably about 100% of the cells, from proliferating in vitro. Thus, desirably the cells are irradiated with a total dose of from about 10,000 to 20,000 rads, optimally, with about 15,000 rads.

Moreover, the cancer antigen, e.g., a cell of the cancer to be treated, i.e., an autologous cancer cell, optimally is treated prior to administration to enhance its immunogenicity. Preferably, this treatment comprises, as described herein, further genetic manipulation, such as, for instance, introduction of other cytokine or immune co-stimulatory functions, or, for example, admixture with nonspecific adjuvants including but not limited to Freund's complete or incomplete adjuvant, emulsions comprised of bacterial and mycobacterial cell wall components, and the like.

In general, the concentration of autologous cancer cells should be sufficient to recruit APCs to the site and result in a greater immune response to the cancer to be treated than would otherwise result in the absence of such treatment. Preferably, at least from about $1 \times 10^6$ to about $1 \times 10^9$ cancer cells, even more preferably, from about $1 \times 10^7$ to about $5 \times 10^8$ cancer cells are used. However, more or less cells can be used depending on the route of administration and the presence of other active agents; etc.

The ratio of bystander cells to autologous cancer cells in a given administration should be such that a benefit due to the presence of the immunomodulatory cytokine-producing bystander cell is realized. With respect to GM-CSF-producing bystander cells, the ratio of bystander cells to autologous cancer cells in a given administration should be such that at least 36 ng GM-CSF/$10^6$ cells/24 hrs is produced. Anti-cancer immunity falls off if the quantity of GM-CSF is less than this. Cytokine levels above this quantity do not further enhance efficacy. In addition to the GM-CSF threshold, the ratio of bystander cells to autologous cancer cells should not be greater than 1:1; otherwise, the overall efficacy of the immune response is impaired. Appropriate ratios of bystander cells to isolated cancer antigens can likewise be determined using routine methods in the art.

One skilled in the art also is aware of means to monitor a therapeutic (i.e., systemic immune) response upon administering a composition of the present invention. In particular, the therapeutic response can be assessed by monitoring attenuation of tumor growth and/or tumor regression. The attenuation of tumor growth or tumor regression in response to treatment can be monitored using several end-points known to those skilled in the art including, for instance, number of tumors, tumor mass or size, or reduction/prevention of metastasis. These described methods are by no means all-inclusive, and further methods to suit the specific application will be apparent to the ordinary skilled artisan.

Any type of cancer can be treated in accordance with the present inventive method. "Cancer" as used herein includes cancers, in particular those of epithelial origin, characterized by abnormal cellular proliferation and the absence of contact inhibition, which can be evidenced by tumor formation. The term encompasses cancer localized in tumors, as well as cancer not localized in tumors, such as, for instance, cancer cells that expand from a tumor locally by invasion. Thus, the method has applicability as a local adjuvant therapy for resected cancers as well as a local control of tumor growth, such as carcinomas of the bladder, breast, colon, kidney, liver, lung, ovary, pancreas, rectum and stomach, and as a treatment of a sarcoma, e.g., fibrosarcoma or rhabdosarcoma, a hematopoietic tumor of lymphoid or myeloid lineage, or another tumor, including, but not limited to, a melanoma, teratocarcinoma, neuroblastoma, or glioma.

The method of the present invention can be combined with other methods of cancer treatment. Examples of such methods include radiation, surgery and chemotherapy. In addition, the method of the present invention can be adapted for non-human mammals, for example, by employing a nonhuman mammalian cell line to generate the universal bystander cell line and a non-human mammalian source of an immunomodulatory cytokine.

The immunomodulatory cytokine-expressing bystander cell line of the present invention also can be used to suppress autoimmune disease, e.g., rheumatoid arthritis, multiple sclerosis; etc. In addition, the bystander cell line of the present invention can be used to enhance an immune response to an infectious disease, such as HIV infection, AIDS and malaria; etc., graft vs. host rejection, and graft rejection.

EXAMPLES

The following examples serve to illustrate the present invention and are not intended to limit its scope.

Example 1

This example describes the manufacture of a universal immunomodulatory cytokine-expressing bystander cell line.

The human GM-CSF gene was cloned by PCR from human peripheral blood. The PCR product was cloned into the Hin dIII-Not I sites in the vector pCEP4 (Invitrogen, Carlsbad, Calif.), which utilizes the human CMV promoter and also encodes hygromycin resistance as a selectable marker. The EBNA-1 portion of this construct was excised by digestion with the restriction enzymes Cla I and Avr II.

The linearized plasmid was used to electroporate the human cell line K562. Drug-resistant cells were initially selected in the presence of hygromycin at 400 µg/ml. After stable transfectants were obtained, the bulk culture was assessed for the production of human GM-CSF using an ELISA assay. The GM-CSF-producing bulk culture was then selected in increasing concentrations of hygromycin, up to a maximal dose of 1200.mu.g/ml. Cells that were resistant to the high dose of hygromycin were subcloned in the presence of 1200 µg/ml hygromycin. Individual subclones were expanded and then tested for the quantity of GM-CSF produced per million cells per 24 hours by ELISA, using the R&D Quantikine Kit (R & D, Minneapolis, Minn.). The results are shown in FIG. 1, which is a bar graph of ng GM-CSF/$10^6$ cells/24 hrs versus cell line. The subclones of K562 produced in excess of 1,000 ng/$10^6$ cells/24 hrs. Subclones that produced the highest quantities of GM-CSF on a per cell basis were subsequently adapted to culture in 100% AIM-V medium (Life Technologies/GIBCO, Gaithersburg, Md.) in the absence of any fetal bovine serum. Cells continued to produce GM-CSF for at least four days after irradiation.

Figure 2A:
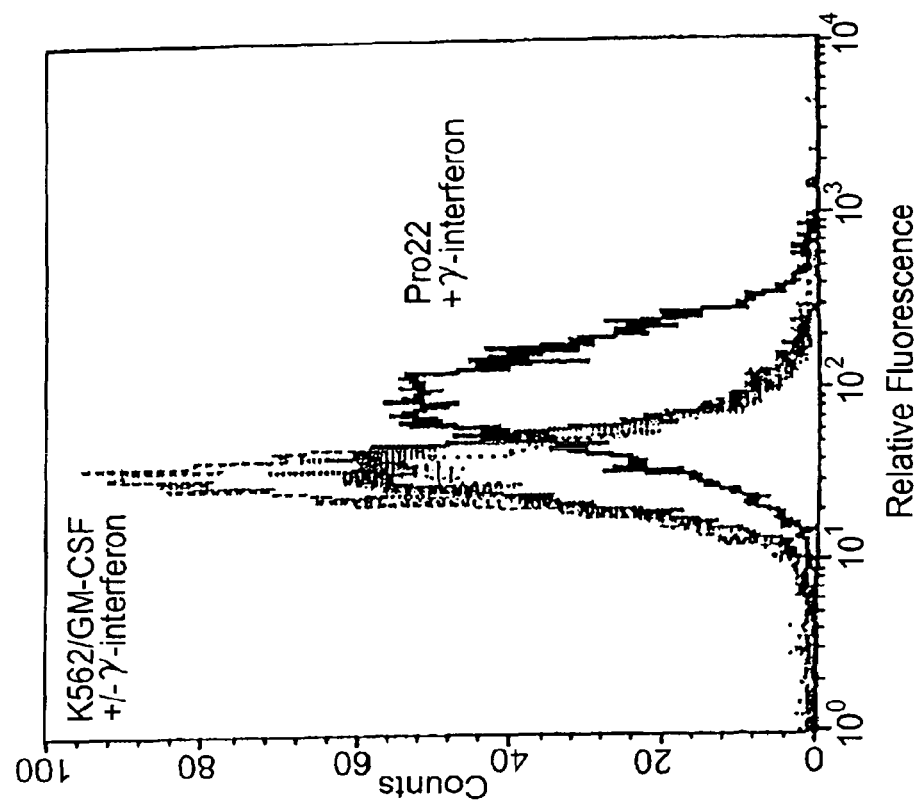
FIG. 2A is a graph of counts versus relative fluorescence for MHC-I antigen expression.
Figure 2B:
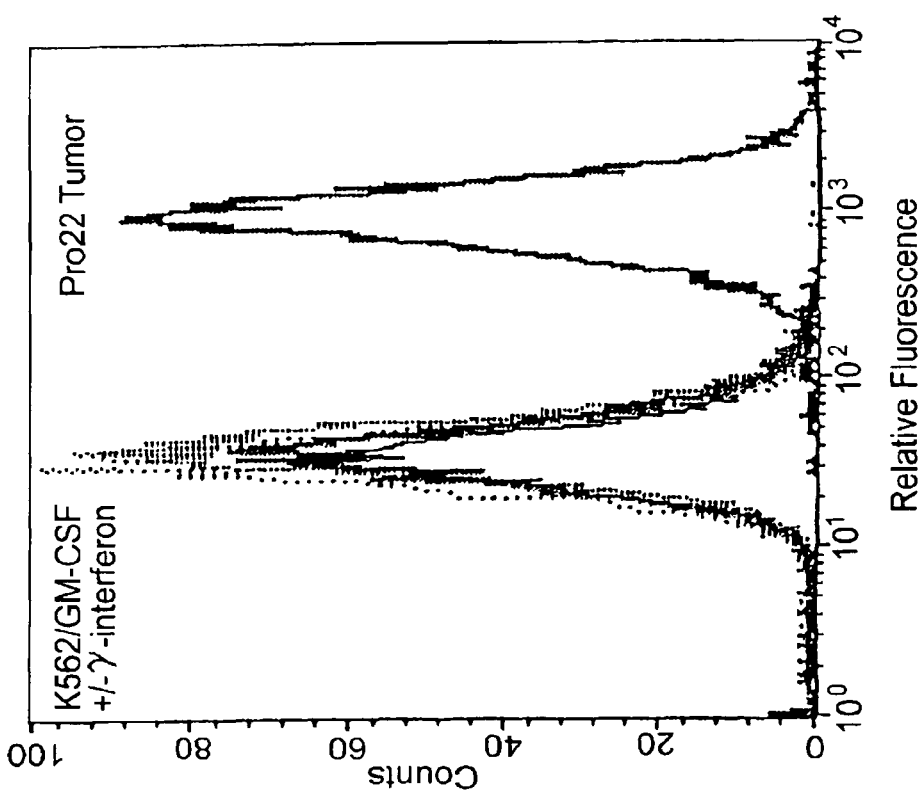
FIG. 2B is a graph of counts versus relative fluorescence for MHC-II antigen expression.

The resulting cell populations were characterized with regard to the expression of HLA Class I and Class II Molecules. GM-CSF-expressing K562 cells and cells obtained from a human prostate carcinoma cell line (obtained from a patient and immortalized; Pro 22, Johns Hopkins University, Baltimore Md.) were cultured in either medium alone or medium supplemented with human recombinant IFNγ (100 units/ml.times.24 hrs). Cells were stained with the primary monoclonal antibodies W632 (anti-human class I heavy chain), L243 (anti-human class II), or mAb14.4.4 (anti-mouse I-E$^d$, an isotype-matched irrelevant control antibody). Cells were then stained with the secondary antibody goat anti-mouse IgG2aFITC (Caltag, Burlingame, Calif.). Ten thousand gated events were collected on a FACScan (Becton Dickinson, San Jose, Calif.) and data were analyzed using the CellQuest software package. The differences in expression in MHC-I and MHC-II antigens between the GM-CSF-expressing K562 cells and the Pro 22 cells are shown in FIG. 2A and FIG. 2B, respectively, which are graphs of counts versus relative fluorescence.

Figure 3:
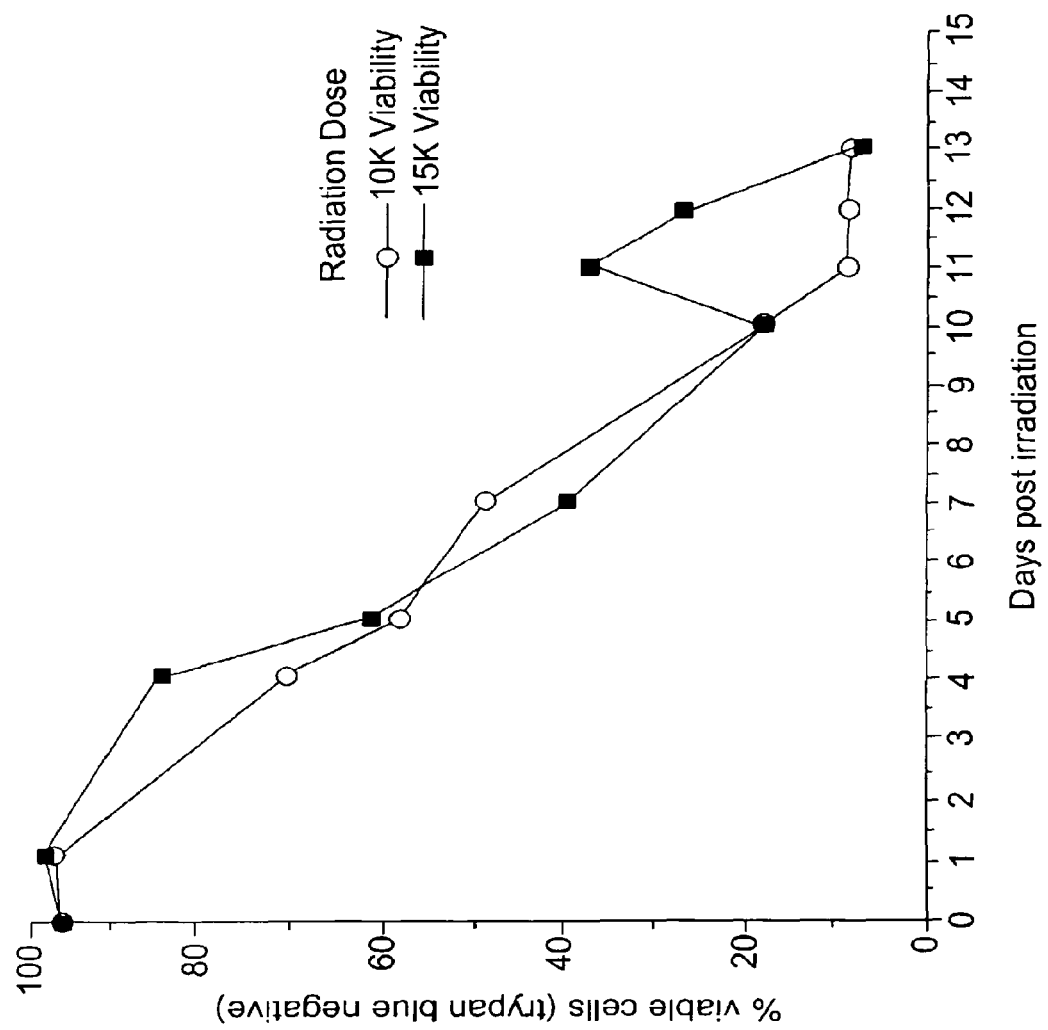
FIG. 3 is a graph of percent (%) viable cells (trypan blue negative) versus days post-irradiation.

The resulting cell populations were also characterized for their sensitivity to ionizing radiation. GM-CSF-expressing K562 cells were irradiated with either 10,000 or 15,000 rads via a cesium gamma irradiator and then $2.5 \times 10^6$ cells of each were placed in culture in 15 mls of medium. Cells were counted and the percent of trypan blue negative cells was recorded. The results are shown in FIG. 3, which is a graph of % viable cells (trypan blue negative) versus days post-irradiation.

Example 2

This example describes the ratio of universal bystander cells to autologous tumor cells to be used in a composition in accordance with the present invention.

Figure 4:
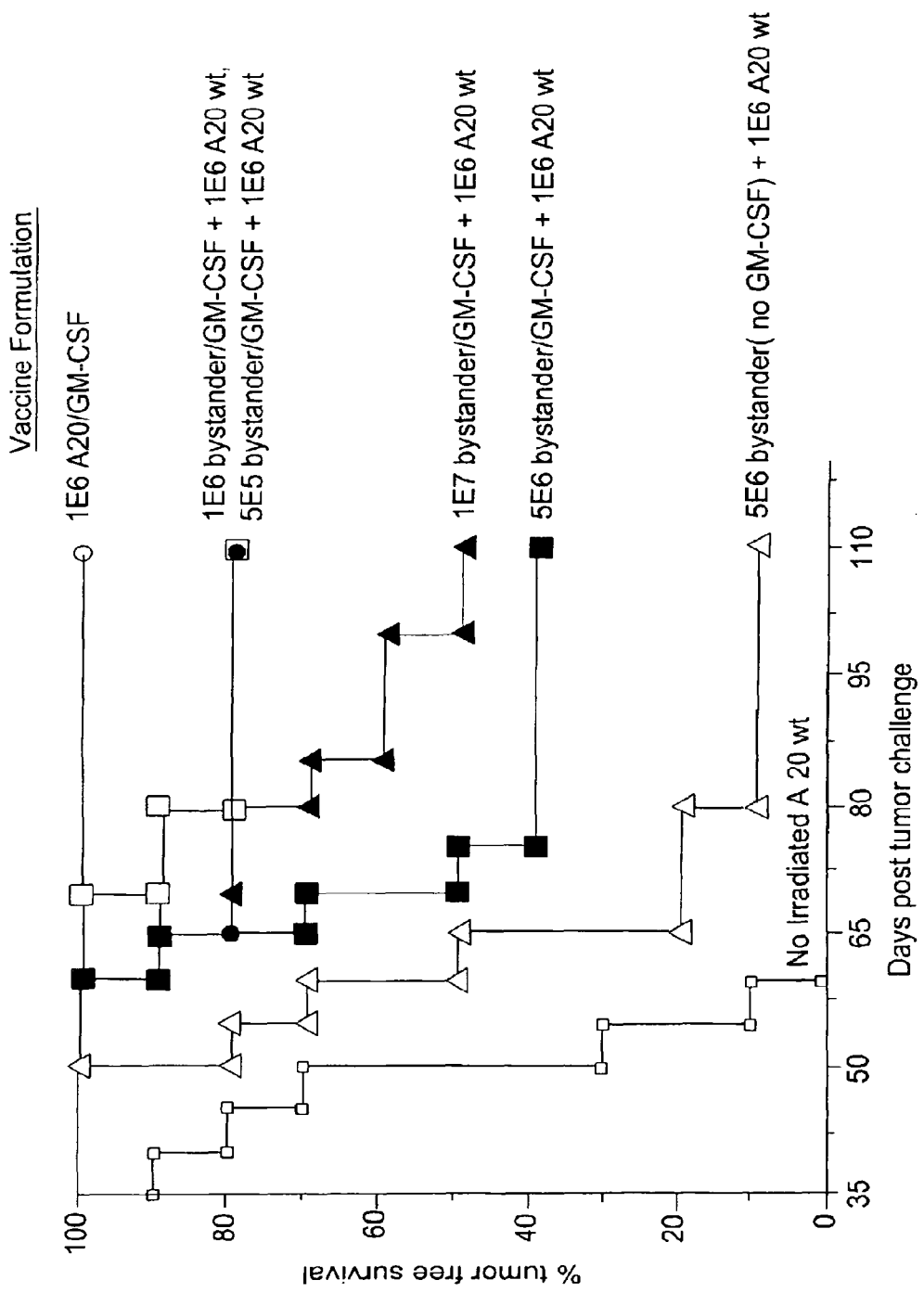
FIG. 4 is a graph of % tumor-free survival versus days post-tumor challenge.

A composition in accordance with the present invention must contain a sufficient number of bystander cells to ensure that at least 36 ng GM-CSF/$10^6$ cells/24 hrs is produced. In addition, the ratio of bystander cells to tumor cells must not be greater than 1:1; otherwise, the overall efficacy of the immune response will be impaired. BALB/c mice were injected intravenously with $1 \times 10^5$ live A20 wild-type cells (NCI, Bethesda, Md.) on day zero. Five days later, mice were immunized subcutaneously with the composition indicated in FIG. 4, which is a graph of % tumor-free survival versus days post-tumor challenge. Allogeneic bystander cells were derived from a C3H(H-2k) lymphoma transduced with a retrovirus (MFG) encoding mouse GM-CSF, which produced 100 ng/$10^6$ cells/24 hrs. A20 cells were transduced with the same construct, resulting in 130 ng GM-CSF/$10^6$ cells/24 hrs. Cells used in all compositions were irradiated with 5,000 rads prior to injection.

As shown in FIG. 1, subclones of GM-CSF-producing K562 cells produced in excess of 1,000 ng/$10^6$ cells/24 hrs. The use of such subclones enables the use of as few as one bystander cell per 10 autologous tumor cells with a clear margin of safety above the GM-CSF threshold of 36 ng GM-CSF/$10^6$ cells/24 hrs, by targeting 100 ng/$10^6$ cells/24 hrs.

All of the references cited herein, including patents, patent applications and publications, are hereby incorporated in their entireties by reference.

While this invention has been described with an emphasis upon preferred embodiments, it will be obvious to those of ordinary skill in the art that variations of the preferred embodiments can be used and that it is intended that the invention can be practiced otherwise than as specifically described herein. Accordingly, this invention includes all modifications encompassed within the spirit and scope of the invention as defined by the following claims.

The invention claimed is:

1. A universal bystander cell line, which: (i) is the human cell line K562 or a subclone thereof, which is modified to lack major histocompatibility class I (MHC-I) antigens and major histocompatibility class II (MHC-II) antigens, and (ii) is modified by introduction of a nucleic acid molecule comprising a nucleic acid sequence encoding an immunomodulatory cytokine operably linked to an inducible promoter, wherein the universal bystander cell line expresses about 500 ng or greater of the immunomodulatory cytokine/$10^6$ cells/24 hours upon being induced.

2. The universal bystander cell line of claim 1, wherein the immunomodulatory cytokine is selected from the group consisting of granulocyte macrophage-colony stimulating factor (GM-CSF) and interleukin-2.

3. The universal bystander cell line of claim 1, wherein the inducible promoter is selected from the group consisting of the IL-8 promoter and the 6-16 promoter.

4. The universal bystander cell line of claim 1, wherein the immunomodulatory cytokine is granulocyte macrophage-colony stimulating factor (GM-CSF).

5. The universal bystander cell line of claim 4, which expresses about 1,000 ng or greater GM-CSF/$10^6$ cells/24 hours upon being induced.

6. A composition comprising the universal bystander cell line of claim 4 and a cancer antigen.

7. A composition comprising
a universal bystander cell line, which: (i) is the human cell line K562 or a subclone thereof, which is modified to lack major histocompatibility class I (MHC-I) antigens and major histocompatibility class II (MHC-II) antigens, and (ii) is modified by introduction of a nucleic acid molecule comprising a nucleic acid sequence encoding granulocyte macrophage-colony stimulating factor (GM-CSF) operably linked to a promoter, wherein the universal bystander cell line expresses about 500 ng or greater GM-CSF/$10^6$ cells/24 hours;
a cancer antigen; and
an adjuvant.

8. The composition of claim 7 wherein the cancer antigen is a cell-surface antigen and the universal bystander cell line is genetically modified to express said cell-surface antigen.

9. A method of stimulating an immune response to a cancer in a human patient, which method comprises administering to said patient the composition of claim 7, wherein said cancer antigen is an antigen of said cancer and wherein said composition is irradiated, whereupon administration of said composition, an immune response to said cancer is stimulated.

10. The method of claim 9, wherein said cancer antigen is a cell of said cancer.

11. In a method of cancer immunotherapy, the improvement comprising administering to a human patient having a cancer the composition of claim 7, wherein said cancer antigen is an antigen of said cancer and wherein said composition is irradiated.

12. The composition of claim 7 wherein said promoter is a cytomegalovirus promoter.

13. The composition of claim 12, wherein said universal bystander cell line expresses about 1,000 ng or greater GM-CSF/$10^6$ cells/24 hours.

14. The universal bystander cell line of claim 1, wherein said nucleic acid molecule further comprises a nucleic acid sequence encoding hygromycin resistance operably linked to a promoter and said universal bystander cell line is selected by growth in a culture medium comprising about 400 ug/ml or greater hygromycin.

15. A composition comprising the universal bystander cell line of claim 1 and a cancer antigen.

16. A method of stimulating an immune response to a cancer in a human patient, which method comprises administering to said patient the composition of claim 6, wherein said cancer antigen is an antigen of said cancer and wherein said composition is irradiated, whereupon administration of said composition, an immune response to said cancer is stimulated.

17. The method of claim 16, wherein said cancer antigen is a cell of said cancer.

* * * * *